United States Patent
Kerber

(10) Patent No.: US 9,744,376 B2
(45) Date of Patent: Aug. 29, 2017

(54) LIQUID CONTAINING FILTER AND HAND HELD HEAT LIGHT

(75) Inventor: Thomas Kerber, Stoney Creek (CA)

(73) Assignee: GENESIS HEALTH LIGHT CORPORATION, Hamilton, Ontario (CA)

(*) Notice: Subject to any disclaimer, the term of this patent is extended or adjusted under 35 U.S.C. 154(b) by 1118 days.

(21) Appl. No.: 13/990,384

(22) PCT Filed: Nov. 28, 2011

(86) PCT No.: PCT/CA2011/050738
§ 371 (c)(1),
(2), (4) Date: Sep. 26, 2013

(87) PCT Pub. No.: WO2012/071669
PCT Pub. Date: Jun. 7, 2012

(65) Prior Publication Data
US 2014/0018886 A1    Jan. 16, 2014

Related U.S. Application Data

(60) Provisional application No. 61/418,009, filed on Nov. 30, 2010, provisional application No. 61/417,810, filed on Nov. 29, 2010.

(51) Int. Cl.
*A61N 5/06* (2006.01)
*H05B 3/00* (2006.01)

(52) U.S. Cl.
CPC ......... *A61N 5/0613* (2013.01); *A61N 5/0625* (2013.01); *H05B 3/0033* (2013.01); *A61N 2005/0644* (2013.01); *A61N 2005/0667* (2013.01)

(58) Field of Classification Search
CPC .. F28F 2265/26; F28F 9/0231; F28F 2265/14; F28F 2255/02
See application file for complete search history.

(56) References Cited

U.S. PATENT DOCUMENTS

| 3,813,514 A | 5/1974 | Canty |
| 4,890,208 A | 12/1989 | Izenour |
| 5,664,864 A | 9/1997 | Kuth |
| 5,898,530 A | 4/1999 | Braun |
| 7,130,507 B2 | 10/2006 | Gawalkiewicz et al. |
| 2008/0253010 A1 | 10/2008 | Cruz |

*Primary Examiner* — Lynsey Crandall
*Assistant Examiner* — Dacheng Xie
(74) *Attorney, Agent, or Firm* — One LLP

(57) ABSTRACT

A liquid-containing heat filter for use with a high-intensity light, said liquid-containing heat filter comprising a substantially hollow reservoir for receiving heat-filtering liquid therein, the reservoir comprising a first optically transparent member, a second optically transparent member, and a peripheral frame for receiving and retaining said first optically transparent member and said second optically transparent member, heat-filtering liquid disposed in said substantially hollow reservoir, and a first resiliently deformable member interposed in trapped relation between the first optically transparent member and a first portion of said peripheral frame, wherein, in use, when the heat-filtering liquid in the reservoir raises in temperature due to the heating effect of the high-intensity light, the first resiliently deformable member is compressed to thereby allow the outward movement of the first optically transparent member due to expansion of the heat-filtering liquid.

19 Claims, 5 Drawing Sheets

LIQUID CONTAINING FILTER AND HAND HELD HEAT LIGHT

PRIORITY DOCUMENTS

This application claims priority to U.S. Provisional Patent Application No. 61/417,810 filed Nov. 29, 2010, and U.S. Provisional Patent Application No. 61/418,009 filed Nov. 30, 2010, both entitled "LIQUID-CONTAINING HEAT FILTER", the contents of which are incorporated herein by reference.

TECHNICAL FIELD

The present application relates to a hand held heat light and a liquid-containing heat filter.

BACKGROUND

Heat lights have therapeutic applications when applied to human skin. Some heat lights make use of liquid heat filters to reduce the user's exposure to light with harmful characteristics.

Liquid-containing heat filters for high-intensity lights experience severe changes in temperature due to the intensity of the light they filter. Such a severe change in temperature causes an unacceptable and even dangerous expansion of the housing of the filter, due to the heating and expansion of the liquid. This is particularly important in the event that the liquid-containing heat filter is used on a high-intensity light for health related purposes.

SUMMARY OF THE INVENTION

The present disclosure describes a high-intensity hand held heat light having a liquid-containing heat filter and ventilation system.

In a first aspect, the disclosure is directed to a liquid-containing heat filter for use with a high-intensity light, said liquid-containing heat filter comprising a substantially hollow reservoir for receiving heat-filtering liquid therein, the reservoir comprising a first optically transparent member, a second optically transparent member, and a peripheral frame for receiving and retaining said first optically transparent member and said second optically transparent member, heat-filtering liquid disposed in said substantially hollow reservoir, and a first resiliently deformable member interposed in trapped relation between the first optically transparent member and a first portion of said peripheral frame, wherein, in use, when the heat-filtering liquid in the reservoir raises in temperature due to the heating effect of the high-intensity light, the first resiliently deformable member is compressed to thereby allow the outward movement of the first optically transparent member due to expansion of the heat-filtering liquid.

In another aspect, the reservoir further comprising a spacer for retaining said first optically transparent member and said second optically transparent member in spaced relation one from the other.

In a further aspect, the filter further comprises a second resiliently deformable member interposed in trapped relation between the second optically transparent member and a second portion of the peripheral frame, wherein, in use, when the heat-filtering liquid in the reservoir raises in temperature due to the heating effect of the high-intensity light, the first resiliently deformable member and the second resiliently deformable member are compressed to thereby allow the outward movement of the first optically transparent member and the second optically transparent member due to expansion of the heat-filtering liquid.

In a further aspect, the first resiliently deformable member comprises a silicone O-ring.

In a further aspect, the first resiliently deformable member has a hardness between 60 durometer and 90 durometer.

In a further aspect, the peripheral frame is formed from a heat-conductive material.

In yet a further aspect, the disclosure is directed to a heat light, comprising a core, the core comprising a liquid filter within a front portion of the core, a fan situated within a rear portion of the core, and a heat lamp situated within the core between the filter and the fan; and a casing substantially surrounding the core and defining a plurality of vents, wherein, in use, the fan operates to create airflows through the vents, between the core and the casing, through the exterior surface of the core, and through the interior of the core.

In a further aspect, the core further comprises a heat sink defining the left, right, top and bottom exterior surfaces of the core, the heat sink defining a plurality of openings therethrough for facilitating airflow.

In a further aspect, in use the fan operates to create a first airflow from the front interior of the core, outward through the openings of the heat sink, and rearward along a top channel along the top exterior surface of the core; a second airflow from the front interior of the core, outward through the openings of the heat sink, and rearward along a bottom channel along the bottom exterior surface of the core; a third airflow into the left interior side of the casing through the left side vents, into a left side channel along the left exterior surface of the core; and a fourth airflow into the right interior side of the casing through the left side vents, into a left side channel along the right exterior surface of the core.

In a further aspect, each of the four airflows is directed into the rear interior of the core through openings of the heat sink by means of a wall extending substantially between the interior of the casing and the exterior of the core at a rear portion of the core.

In a further aspect, the light further comprises at least one ridge extending between the casing and an exterior surface of the core for directing airflow.

In a further aspect, the at least one ridge comprises at least one ridge for directing airflow from the space between the casing and the core into the interior of the core.

In a further aspect, the at least one ridge comprises a plurality of ridges for directing airflow into a plurality of channels running toward the rear of the light and defined by the interior of the casing, the exterior of the core, and the plurality of ridges.

In a further aspect, the light further comprises a heat sensor for detecting dangerous levels of heat and deactivating the lamp in response thereto.

In a further aspect, the heat sensor is attached to the peripheral frame of the filter.

In a further aspect, the casing further comprises a circular handle for facilitating use of the light by a user in various positions.

Other example embodiments of the present disclosure will be apparent to those of ordinary skill in the art from a review of the following detailed description in conjunction with the drawings.

BRIEF DESCRIPTION OF THE DRAWINGS

It will be noted that throughout the drawings and description similar features are identified by the same reference numerals.

DETAILED DESCRIPTION OF EXAMPLE EMBODIMENTS

The present disclosure describes a high-intensity hand held heat light having a liquid-containing heat filter and ventilation system. In some embodiments, the liquid-containing heat filter includes one or more resilient members to allow displacement of one or more parts of the liquid reservoir to accompany the expansion of the liquid contained therein. The device also includes in some embodiments a casing having multiple channels for airflow to provide cooling for the lamp and the filter. Some embodiments of the device have a circular handle for facilitating application to the body in various positions. Some embodiments of the device have a heat sensor for shutting down operation when dangerous temperatures are detected.

Figure 1:
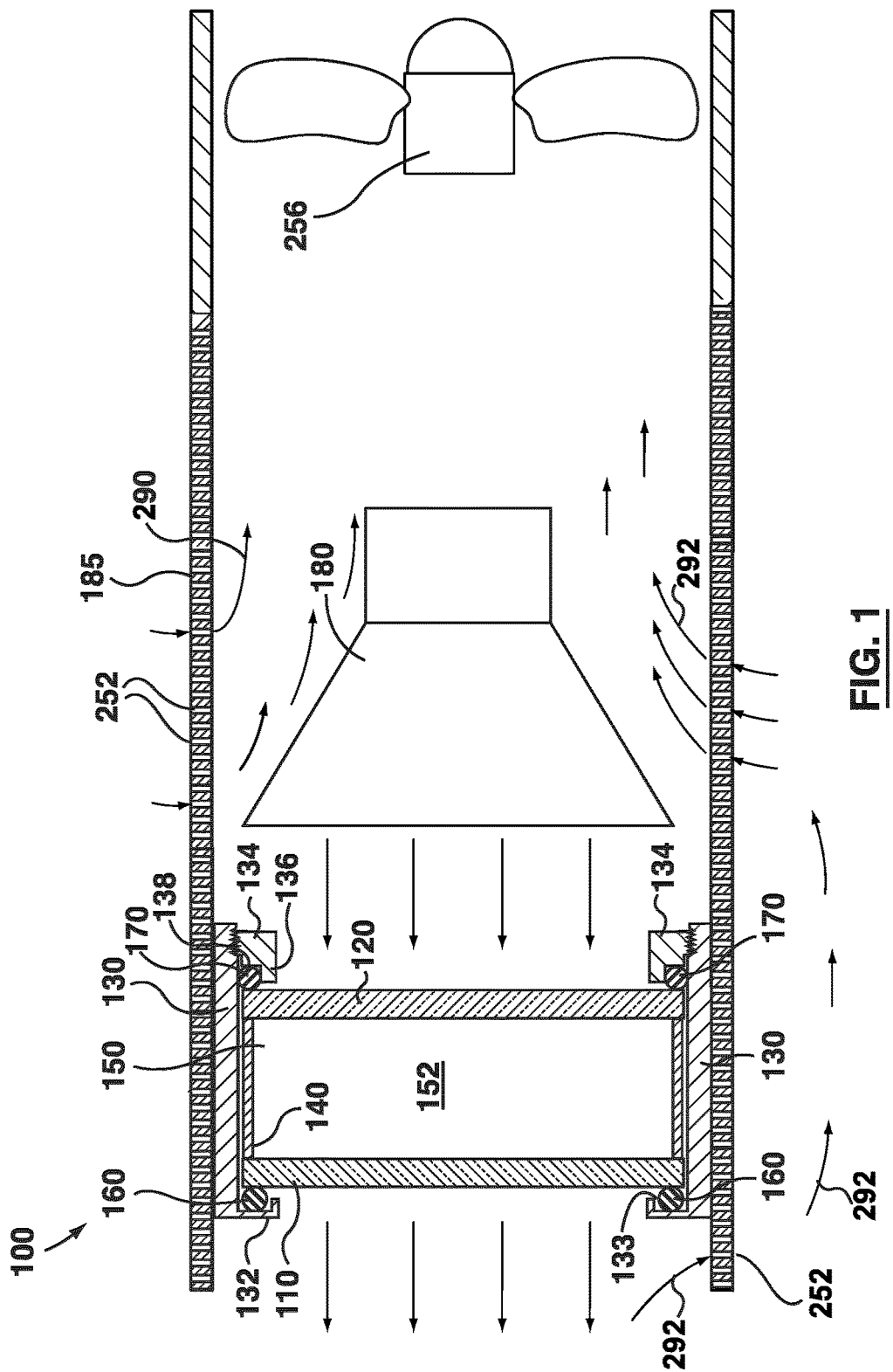
FIG. 1 is a cut-away side elevational view of a liquid-containing heat filter according to an example embodiment, with the liquid-containing heat filter at an ambient temperature.

FIG. 1 shows a liquid-containing heat filter according to an example embodiment. The liquid-containing heat filter 100 is appropriate for use with high-intensity lights. The liquid-containing heat filter 100 comprises a first light passing member which in an example embodiment is an optically transparent member 110 and a second light passing member which in an example embodiment is an optically transparent member 120. In some embodiments, the first optically transparent member 110 and the second optically transparent member 120 each comprise a small sheet or pane of tempered glass. Alternatively, any other suitable material could be used.

There is a peripheral frame 130 for receiving and retaining the first optically transparent member 110 and the second optically transparent member 120. In an example embodiment, the peripheral frame 130 comprises a metal shell frame, specifically a brass shell frame. The peripheral frame 130 comprises a first portion 132 at the front of the peripheral frame 130, which first portion 132 comprises an "L"-shaped lip defining an annular channel 133. The peripheral frame 130 also comprises a second portion 134 at the back of the peripheral frame 130, which second portion 134 comprises a threaded fastener having an outer thread engaged in a co-operating threaded portion in the peripheral frame 130. The threaded fastener 134 has a forwardly extending portion 136 that defines an annular receiving channel 138.

There is also a spacer 140 for retaining the first optically transparent member 110 and the second optically transparent member 120 in spaced relation one from the other. In an example embodiment, the spacer 140 comprises a metal ring having an outside diameter very slightly smaller than the inside diameter of the peripheral frame 130.

The peripheral frame 130, the first optically transparent member 110 and the second optically transparent member 120 together form a substantially hollow reservoir 150 for receiving heat-filtering liquid 152 therein. The heat-filtering liquid 152 is disposed in the substantially hollow reservoir 150. The heat-filtering liquid 152 may remain substantially stationary within the substantially hollow reservoir 150 or may in some embodiments be circulated by an appropriate circulating system.

A first resiliently deformable member 160 is interposed in trapped relation between the first optically transparent member 110 and the first portion 132 of the peripheral frame 130, namely the "L"-shaped lip, within annular channel 133. A second resiliently deformable member 170 interposed in trapped relation between the second optically transparent member 120 and a second portion 134 of the peripheral frame 130, namely the threaded fastener. More specifically, the second resiliently deformable member 170 is received in the annular receiving channel 138.

In some embodiments, the first resiliently deformable member 160 and the second resiliently deformable member 170 are made from a silicone based material having a hardness of between about 60 durometer and about 90 durometer. Some embodiments have a hardness of about 70 durometer. Silicone "O"-rings may be used in some embodiments.

In some embodiments, the first optically transparent member 110 is thicker than the second optically transparent member 120. In the event that the pressure within the substantially hollow reservoir 150 becomes extremely high, the second optically transparent member 120 will shatter instead of the first optically transparent member 110 shattering. Accordingly, if the liquid-containing heat filter 100 is used for medical purposes, or for any reason is used near a person, the thicker first optically transparent member 110 would face the person to ensure safety.

Figure 2:
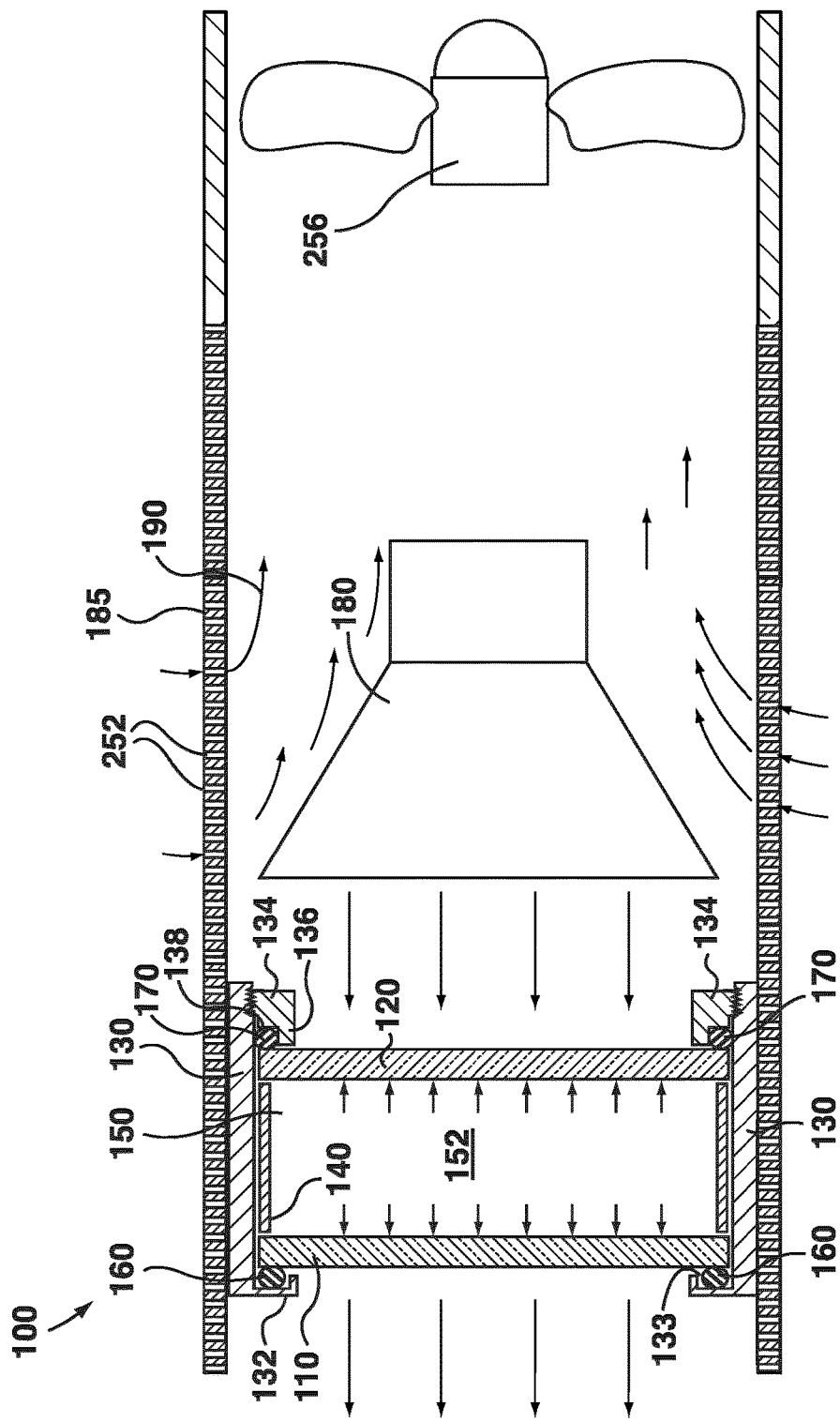
FIG. 2 is a further cut-away side elevational view of the liquid-containing heat filter, with the liquid-containing heat filter at an elevated temperature.

In use, when the heat-filtering liquid 152 in the substantially hollow reservoir 150 raises in temperature due to the heating effect of a high-intensity light or lamp 180, the first resiliently deformable member 160 and the second resiliently deformable member 170 are compressed to thereby allow the outward movement of the first optically transparent member 110 and the second optically transparent member 120 due to expansion of the heat-filtering liquid 152. As shown in FIG. 1, the liquid-containing heat filter 100 is at an ambient temperature. As can be readily seen, the first resiliently deformable member 160 and the second resiliently deformable member 170 are only very slightly deformed. As shown in FIG. 2, the liquid-containing heat filter 100 is at an elevated temperature. Accordingly, the heat-filtering liquid 152 also expands somewhat, as does the tempered glass first optically transparent member 110 and the tempered glass second optically transparent member 120. As can be readily seen, the first resiliently deformable member 160 and the second resiliently deformable member 170 are substantially deformed in order to accommodate that expansion, thus reducing the pressure build up within the substantially hollow reservoir 150.

In some example embodiments, the heat-filtering liquid 152 is water containing an anti-freeze liquid. In some embodiments, the heat-filtering liquid may be coloured to provide additional filtering—for example, red or pink anti-freeze could be applied to water to provide the heat-filtering liquid 152.

Figure 3:
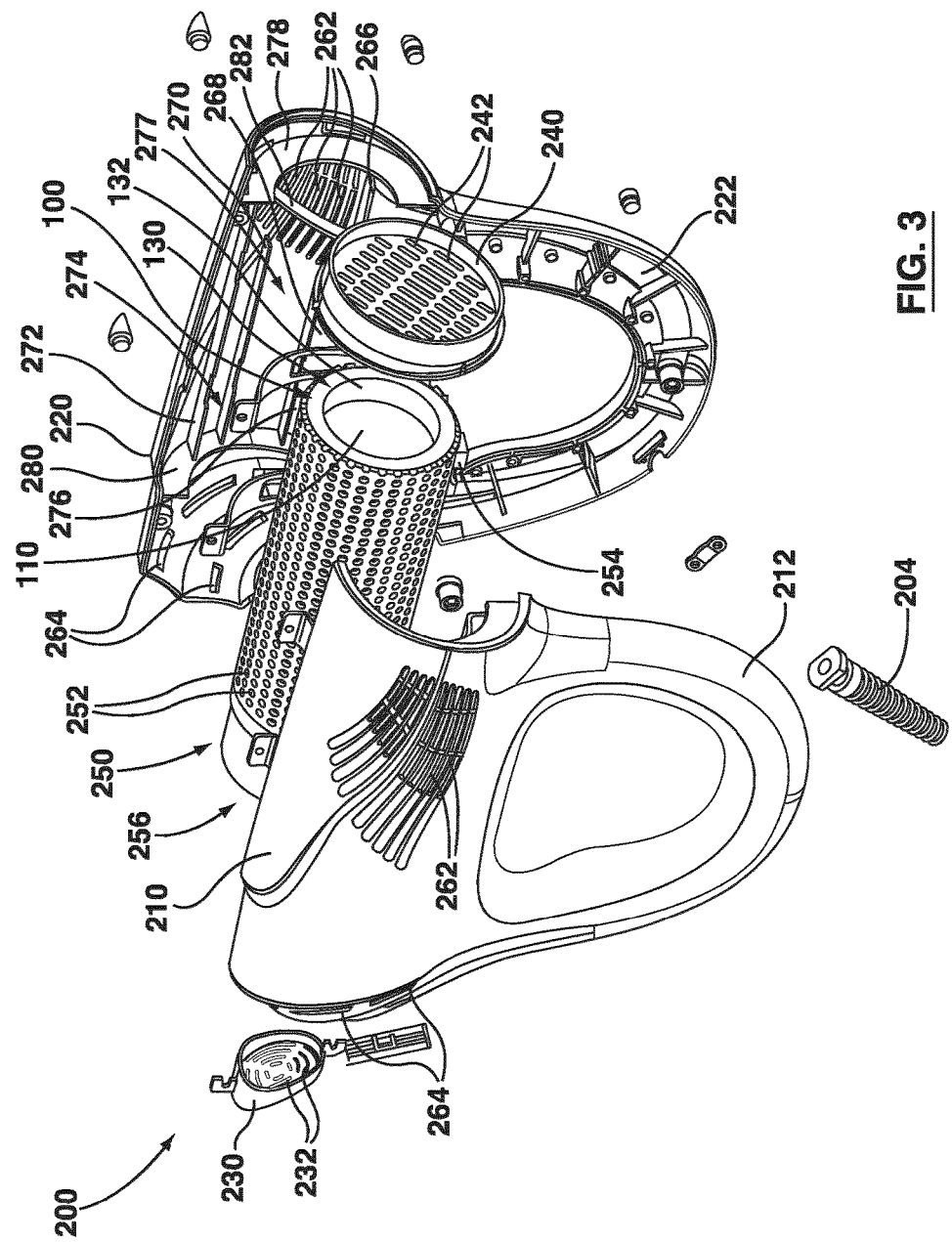
FIG. 3 is an isometric partially exploded view of a hand-held heat light according to an example embodiment.

FIG. 3 shows a hand-held heat light that incorporates the heat filter 100 according to an example embodiment. The heat light 200 includes a lamp 180 and liquid-containing heat filter 100 contained within a substantially cylindrical core 250 that comprises a cylindrical heat sink 185, which in some embodiments is an aluminum heat sink. The lamp 180 is situated with the core 250 behind the heat filter 100, which is situated at the front end of the core 250 facing forward. In some examples, the lamp is a halogen light source. In some embodiments, a fan 256 is situated behind the lamp 180 at the rear of the core 250 and operates to pull air through the heat light 200 to facilitate airflow and cooling. In the illustrated embodiment, the fan 256 operates to pull air from the front and blow air toward the back of the heat light 200.

The illustrated heat light 200 includes an outer casing 205 comprising a left casing 220, a right casing 210, a front casing 240 and a rear casing 230. The casing 205 may be formed from any suitable material, such as a high-impact plastic. The casing 205 includes various vents and holes placed and shaped to facilitate cooling airflow through the device, as further described below. The left casing 220 and right casing 210 include, respectively, a left handle portion 222 and right handle portion 212 that together form a circular handle 202 when the casing 205 is assembled. The circular handle 202 allows a user to hold the device in operation in any of a number of different positions or configurations, thereby facilitating application to different parts of the user's body or the body of another person.

Airflow through the heat light 200 follows several different paths and comes into contact with different components, thereby increasing the cooling effects of the airflow. The fan 256 in conjunction with natural convection currents and other airflow creates a general airflow from the front of the device toward the rear.

Figure 7:
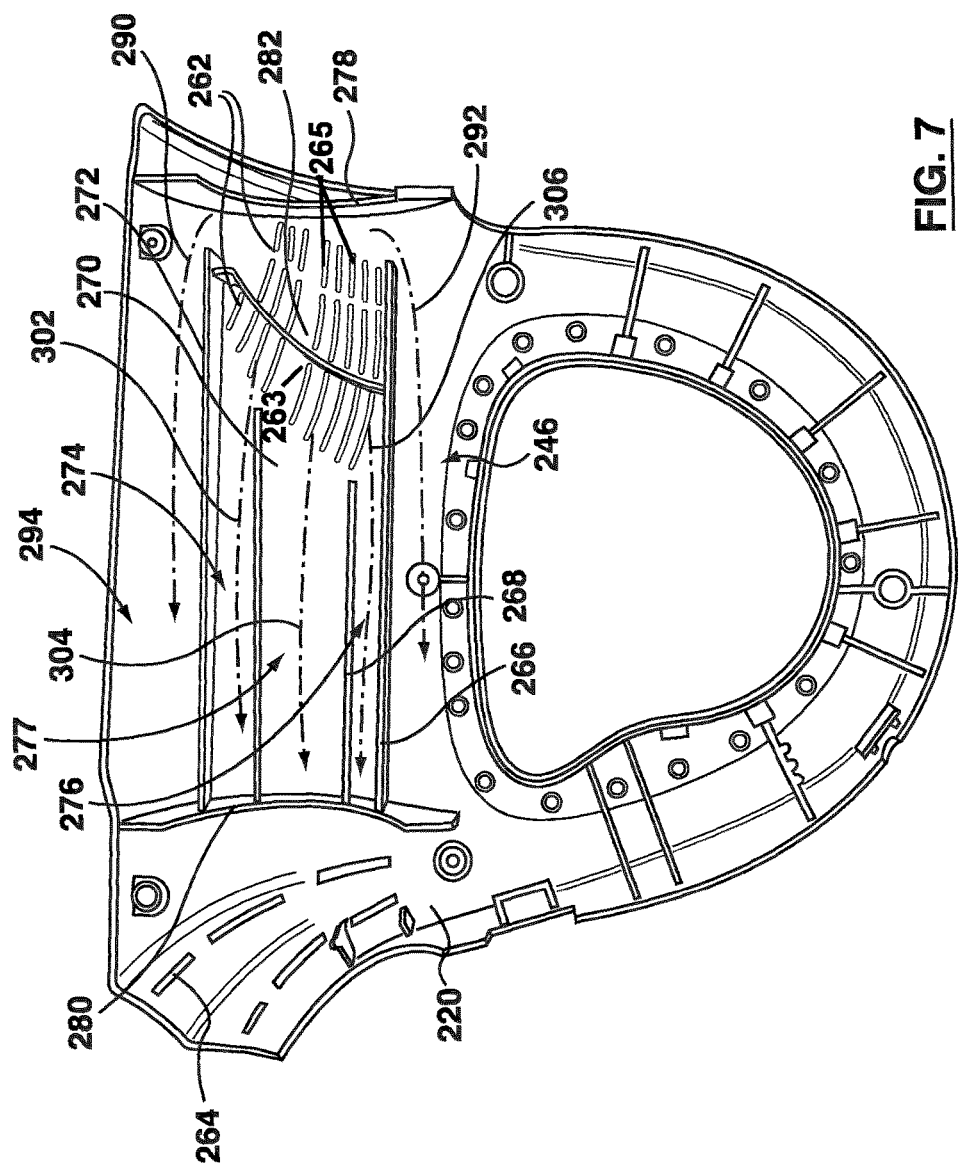
FIG. 7 is a sectional view showing the interior of a left side casing of a hand-held heat light according to an example embodiment showing airflow through the casing.

With reference to FIG. 7, air flows through front side vents 262 in the left casing 220 (air flow in the right casing 210 is substantially identical to air flow in the left casing. In the illustrated embodiment, the front side vents 262 are divided into forward and rearward front vents 265, 263 vertically by a arcuate vertical ridge 282 which extends inward from the casing 205 substantially to the outside surface of the core 250. Other ridges and walls also extend inwardly from the casing 205 to the outside surface of the core 250 in various orientations, including a front wall 278, a back wall 280, and a first horizontal ridge 266, second horizontal ridge 268, third horizontal ridge 270, and fourth horizontal ridge 272 in parallel from bottom to top. The four horizontal ridges 266, 268, 270, 272 extend forward from the back wall 280. The first horizontal ridge 266 and fourth horizontal ridge 272 extend forward to at least the vertical ridge 282 (which in the illustrated embodiment is situated diagonally between the first 266 and fourth 272 horizontal ridges). The second 268 and third 270 horizontal ridges do not extend the full distance to the vertical ridge 282.

Air flowing into the casing 205 through the side vents 263 to the rear of the vertical ridge 282 is split into three side channels running horizontally between the casing 205 and the core 250 defined by the horizontal ridges 266, 268, 270 and 272—in particular, some air creates an upper flow 302 through an upper side channel 274 defined between the fourth 272 and third 270 horizontal ridges, some air creates a middle side flow 304 through a middle side channel 277 defined between the third 270 and second 268 horizontal ridges, and some air creates a lower side flow 306 through a lower side channel 276 defined between the first 266 and second 268 horizontal ridges. These airflows provide cooling to the outside of the heat sink 185. When these airflows reach the back wall 280, they are forced through the holes 252 in the heat sink 185 into the interior of the core 250 and thence through the fan 256. Longitudinal side airflow channels identical to channels 274, 302 and 306 are also provided on the right side of the core 250.

In addition to the side channels 274, 276, 277 described above, airflow is also created through a top channel 294 above the fourth horizontal ridge 272 and a bottom channel 296 below the first horizontal ridge 266. At least some of the air flowing through these upper and lower channels first passes through through holes 242 in the front casing 240 (Holes 242 also allow light from the lamp 180 to pass through the front casing 240 more effectively). This airflow passes through the front casing holes 242, into the front portion of the heat sink 185 projecting forward from the filter 100. Airflow through front casing holes 242 provides cooling to the front portion of the heat sink 185 and filter 100—this airflow splits into a top airflow 290 and a bottom airflow 292, passing outward through the front end heat sink 185 by means of holes 252 in the heat sink 185 and continuing between the casing 205 and the core 250 through the top channel 294 and bottom channel 296, providing cooling to the top and bottom exterior surfaces of the heat sink 185. Like the side channel airflows described above, when the top and bottom channel airflows reach the back wall 280, they are forced through the holes 252 in the heat sink 185 into the interior of the core 250 and thence through the fan 256. The air inside the front portion of the heat sink 185 is not pulled into the side channels 174, 176, 177, as such a path would be blocked by the vertical ridge 282. Air flowing into the casing 205 through the side vents 265 forward of the vertical ridge 282 also is directed into upper and lower airflow channels 294, 296, thereby ensuring that air flows across the front end of the heat sink 185 and filter 100 even if front casing opening 252 are blocked off (for example, by being pressed against a user's skin).

Accordingly, the device provides two main airflows in parallel: a first set of side airflows 274, 276, 277 through the rearward forward side vents 263 and along the left and right sides of the heat sink 185, and a second set of top and bottom airflows 290, 292 through the front holes 242, out through the holes 252 in the heat sink 185, and along the top channel 294 and bottom channel 296 along the top and bottom sides of the heat sink 185 (see also FIG. 1). Forward side slots 265 also contribute to the airflow through the top and bottom airflow paths 290, 292. Both sets of airflows are pulled back into the interior of the core before reaching the back wall 280 and expelled to the rear of the core 250 by the fan 256.

Air flowing out through the back of the fan 256 is forced out of rear side vents 264 in the left casing 220 and right casing 210 and through holes 232 in the rear casing 230. The back wall 280 ensures that the fan is able to create suction through the entire device by blocking side channels.

In some embodiments, some airflow may also be created as air in the interior of the core 250 flows outward through the holes 250 in the heat sink 185 to lower-pressure side channels 302, 304, 306, top channel 294, and bottom channel 296 before being pulled back into the core 250 closer to the back wall 280. This airflow may increase the effectiveness of the heat sink 185 by increasing the airflow through its many holes 252 and over its inner and outer surfaces.

Figure 6:
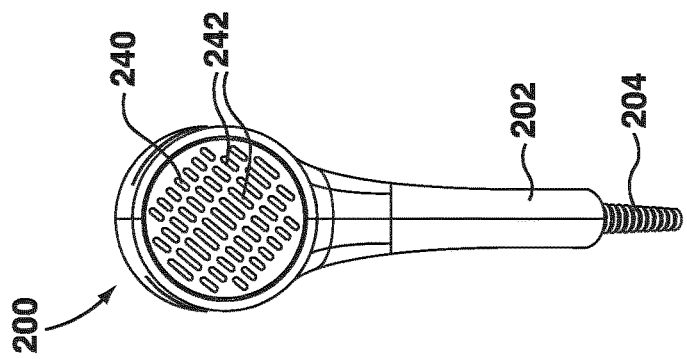
FIG. 6 is a front view of a hand-held heat light according to an example embodiment.
Figure 5:
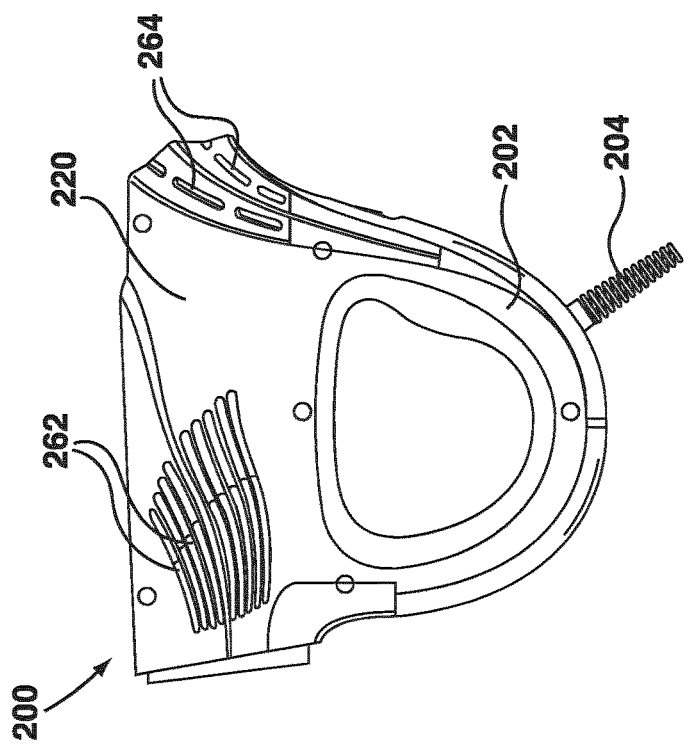
FIG. 5 is a left side view of a hand-held heat light according to an example embodiment.
Figure 4:
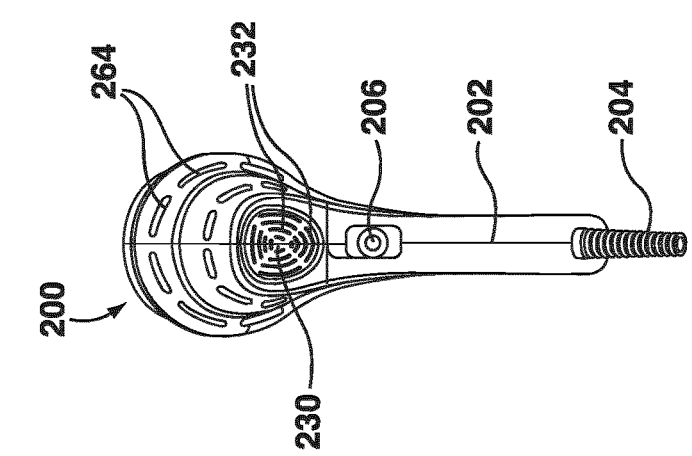
FIG. 4 is a rear view of a hand-held heat light according to an example embodiment.

The assembled outer casing 205 is shown in rear, side, and front views in FIGS. 4, 5, and 6 respectively. The illustrated embodiment has a power cord 204 for carrying power to the device, and a power switch 206 for activating and deactivating the lamp 180 and fan 256.

Some embodiments include a heat sensor 254. The heat sensor in the illustrated embodiment of FIG. 3 is attached to the underside of the filter 100, on the outside of the peripheral frame 130. Where the peripheral frame 130 is a heat-conductive material such as brass, the heat sensor 254 is situated to detect dangerous levels of heat on the exterior of the filter 100 and to respond thereto. In some embodiments, the sensor 254 is interconnected to the electrical power system of the heat light 200 and cuts off power to the lamp 180 when a predetermined heat threshold is detected. In some embodiments, the fan 256 may also be deactivated.

The circular handle 202 may in some embodiments be formed fully or partially from a different material from the casing 205, such as a gripping rubber material, for ease of handling.

The example embodiments of the present disclosure described above are intended to be examples only. Those of skill in the art may effect alterations, modifications and variations to the particular embodiments without departing from the intended scope of the present disclosure. In particular, features from one or more of the above-described example embodiments may be selected to create alternate example embodiments included of a sub-combination of features which may not be explicitly described above. In addition, features from one or more of the above-described example embodiments may be selected and combined to create alternate example embodiments included of a combination of features which may not be explicitly described above. Features suitable for such combinations and sub-combinations would be readily apparent to persons skilled in the art upon review of the present disclosure as a whole. The subject matter described herein and in the recited claims intends to cover and embrace all suitable changes in technology.

The invention claimed is:

1. A liquid-containing heat filter for use with a high-intensity light, said liquid-containing heat filter comprising:
   a substantially hollow reservoir for receiving heat-filtering liquid therein, comprising:
   a first light passing member;
   a second light passing member; and
   a peripheral frame for receiving and retaining said first light passing member and said second light passing member;
   the heat-filtering liquid disposed in said substantially hollow reservoir; and
   a first resiliently deformable member interposed in a trapped relation between the first light passing member and a first portion of said peripheral frame,
   wherein the first resiliently deformable member is configured to compress when the first light passing member moves outwardly as a result of an expansion of the heat-filtering liquid due to a rise in temperature through emission of the high-intensity light on the heat-filtering liquid.

2. The filter of claim 1, the reservoir further comprising a spacer for retaining said first light passing member and said second light passing member in spaced relation one from the other.

3. The filter of claim 1, further comprising a second resiliently deformable member interposed in a trapped relation between the second light passing member and a second portion of the peripheral frame,
   wherein the second resiliently deformable member is configured to compress when the second light passing member moves outwardly as a result of an expansion of the heat-filtering liquid due to a rise in temperature through emission of the high-intensity light on the heat-filtering liquid.

4. The filter of claim 1 wherein the first resiliently deformable member comprises a silicone O-ring.

5. The filter of claim 1 wherein the first resiliently deformable member has a hardness between 60 durometer and 90 durometer.

6. The filter of claim 1 wherein the peripheral frame is formed from a heat-conductive material.

7. The filter of claim 1 wherein the first light passing member and the second light passing member are each optically transparent members.

8. The filter of claim 1 wherein the heat-filtering liquid is water containing anti-freeze.

9. The filter of claim 1 wherein one of the first and second light passing members has a lower pressure failure threshold than the other of the first and second light passing members such that any failure of the filter will be directed in a predetermined direction.

10. The filter of claim 1 wherein the peripheral frame defines a threaded portion at an end thereof receiving a threaded ring, the first resiliently deformable member interposed in a trapped relation between the first light passing member and the threaded ring.

11. A heat light, comprising:
    a core comprising:
       the filter according to claim 1 situated within a front portion of the core;
       a fan situated within a rear portion of the core; and
       a high-intensity light situated within the core between the filter and the fan and directed to provide light towards the filter; and
    a casing substantially surrounding the core and defining a first plurality of vents,
    wherein, in use, the fan operates to create airflows through the first plurality of vents, between the core and the casing, through the exterior surface of the core, and through the interior of the core.

12. The heat light of claim 11, comprising a heat sink defining at least a portion of core, the heat sink defining a plurality of openings therethrough for facilitating airflow.

13. The heat light of claim 12, wherein the casing and core define there between at least a first airflow path and a second airflow path at a front portion of the heat light, and in use the fan operates to create:
    a first airflow through the first airflow path, at least a portion of the second airflow entering through a front facing opening defined by the casing forward of the filter, the first airflow flowing rearward within the casing;
    a second airflow through the second airflow path, at least a portion of the second airflow entering the casing through at least some of the first plurality of vents in the casing and flowing rearward over a surface of the core.

14. The heat light of claim 13 wherein the casing includes at least one inwardly projecting wall or ridge that defines a boundary between the first and second airflow paths.

15. The heat light of claim 14 wherein the casing includes a second plurality of vents on the casing forward of the first plurality of vents, the second plurality of vents providing airflow to the first airflow path.

16. The heat light of claim 15 wherein the heat sink extends forward of the filter, wherein at least a portion of the first airflow passes into the casing through the front facing opening, then passes from an interior to an exterior of the heat sink through a plurality of the heat sink openings to pass over an exterior of the filter and high-intensity light then passes back into an interior of the heat sink rearward of the high-intensity light.

17. The heat light of claim 11 further comprising a heat sensor attached to the filter for detecting dangerous levels of heat and deactivating the high-intensity light in response thereto.

18. The heat light of claim 11 casing comprising a circular handle for facilitating use of the heat light by a user in various positions.

19. The heat light of claim 11 wherein the first light passing member located at a front end of the core is thicker than the second light passing member facing the high-intensity light.

* * * * *